United States Patent [19]
Watanabe et al.

[11] Patent Number: 5,112,869
[45] Date of Patent: May 12, 1992

[54] SUBSTITUTED 1-PHENYLNAPHTHALENES

[75] Inventors: Kyoichi A. Watanabe, Rye Brook; Tsann-Long Su, Somers; Jai-Tung Huang, Mamaroneck, all of N.Y.

[73] Assignee: Sloan-Kettering Institute For Cancer Research, New York, N.Y.

[21] Appl. No.: 332,893

[22] Filed: Apr. 4, 1989

[51] Int. Cl.$^5$ ................. A61K 31/13; C07C 251/24
[52] U.S. Cl. ........................ 514/641; 564/270; 568/632; 568/633; 568/441; 568/734; 568/737; 568/808; 514/811; 514/842; 514/883; 514/908; 514/700; 514/717; 514/721; 514/732; 514/843
[58] Field of Search ............ 564/270; 568/632, 633, 568/441, 734, 735, 737, 808; 534/838; 514/841, 842, 843, 883, 908, 700, 717, 721, 732, 765, 641

[56] References Cited

U.S. PATENT DOCUMENTS 4,297,341 10/1981 Waller et al. .................... 514/700

FOREIGN PATENT DOCUMENTS 298466 1/1989 European Pat. Off. ............ 568/441
2075496 11/1981 United Kingdom ................ 568/633

OTHER PUBLICATIONS

Carmichael, I., *Chemical Abstracts*, 110:94360g (1989), Abstract of *J. Phys. Chem. Ref. Data*, 15(1), pp. 1–250 (1986).
P. Robins et al., *J. Chem. Soc.*, Part I, "A New and Specific Aromatisation Reaction," pp. 409–421 (1958).
Sonenberg et al., *Chemical Abstracts* 109:17147v, Abstract of *Contraception*, 37(3), 247–55 (1988).
Rao, P.N., *Cancer Chemother. Pharmacol.*, 15, pp. 20–25 (1985).
Heller et al., *Chemical Abstracts* 108:206,269b, p. 86 (1988).
K. Buggle et al., *Chemical Abstracts* 99:212253d, p. 618 (1983).
I. Repinskaya et al., *Chemical Abstracts* 104:50602j, p. 493 (1986).
S. Lee et al., *Chemical Abstracts* 98:53354y, p. 621 (1983).
Tuszynski, G. and Cossu, G., *Cancer Research*, pp. 768–771 (1984).
Wichmann, K. et al., *J. Reprod. Fert.*, pp. 259–264 (1983).
Kim, S. et al., *Cancer Research*, vol. 45, pp. 6338–6340 (1985).
Montamat, E. et al., *Science*, vol. 18, pp. 288–289 (1983).

(List continued on next page.)

*Primary Examiner*—Richard L. Raymond
*Assistant Examiner*—Mark W. Russell
*Attorney, Agent, or Firm*—John P. White

[57] ABSTRACT

This invention concerns compounds having the structure:

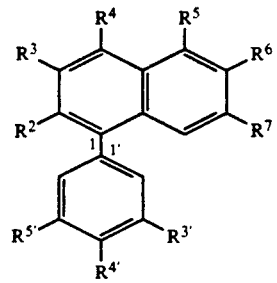

wherein each of $R^2$, $R^3$, $R^4$, $R^5$, $R^6$, $R^7$, $R^{2'}$, $R^{3'}$, $R^{4'}$, and $R^{5'}$, is independently hydrogen (—H), or a hydroxyl (—OH), methoxy (—OMe), methyl (—Me), carboxaldehyde (—CHO) or phenylformazen (Ph—N=CH—) group.

This invention also provides a novel process of synthesizing the compounds of the subject invention, including intermediate compounds useful in the process.

The present invention also provides pharmaceutical compositions comprising a pharmaceutically effective amount of a compound according to the subject invention and a pharmaceutically acceptable carrier. Finally, the invention provides spermicidal methods and methods of killing or of retarding the proliferation of, cancer cells.

13 Claims, 1 Drawing Sheet

OTHER PUBLICATIONS

Poso, H. et al., Lancet, Apr. 19, 1980, p. 885 (1980).
Edwards, J., J. Am. Chem. Soc., vol. 80, pp. 3798–3799 (1958).
Heidrich, J. et al., IRCS Med. Sci., vol. 11, p. 304 (1983).
Jolad, S. et al., J. Pharma. Sci., vol. 64, pp. 1889–1890 (1975).
Sonenberg, M. et al., Contraception, vol. 37, No. 3, pp. 247–255 (1988).
Adams, R. et al., J. Am. Chem. Soc., vol. 60, pp. 2193–2204 (1938).
Dorset, P. and Kerstine, E., J. Pharma. Sci., vol. 64, pp. 1073–1075 (1975).
E. Campaigne et al., *Chemical Abstracts 107:7022u, p. 646 (1987)*.

SUBSTITUTED 1-PHENYLNAPHTHALENES

The invention described herein was made in the course of work under grants nos. CA-08748 and CA-18856 from the National Cancer Institute, National Institutes of Health, U.S. Department of Health and Human Services.

BACKGROUND OF THE INVENTION

Gossypol, a complicated dimer of sesquiterpene with multiple biological activities, was isolated from certain species of the cotton plant. The chemical structure was first identified by Adams in 1938 [Adams, R., R. C. Morris, T. A. Geissman, D. J. Butterbaugh, and E. C. Kirkpatrick, J. Am. Chem. Soc., 60:2193 (1938)]and was confirmed by Edwards in 1958 by total synthesis Edwards, J. D., J. Am. Chem. Soc., 80:3798 (1958)].

In recent years, there has been an increased interest in gossypol, due mainly to reports from China that this natural product was identified as the principal agent of the cottonseed oil which causes infertility [National Coordinating Group on Male Antifertility Agents, Chin. Med. J., 4:417 (1978)]. Gossypol has since been reported to exhibit spermicidal effects in vitro [Poso, H., K. Wichmann, J. Janne, and T. Luukkainen. Lancet, 885 (1980)]by inhibition of lactate dehydrogenase X and hence, ATP production [Wichmann, K., K. Kapyaho, R. Sinervirta, and J. Janne, J. Reprod. Fert., 69: 259 (1983)].

Gossypol has been reported to inactivate the enveloped viruses such as parainfluenza type 3 and Herpes simplex viruses [Dorsett, P. H., and E. E. Kerstine, J. Pharm. Sci., 64: 1073 (1975)]. Montamat et al., reported that this natural product was effective in reducing the growth of *Trypansoma cruzi*, the causative agent of Chaga's disease for which there is no satisfactory drug [Montamat, E. E., C. Burgos, N. M. G. de Burgos, L. E. Rovari, A. Blanco, and E. L. Segura, Science, 218: 288 (1982)]. Human malarial parasite *Plasmodium falciparum* is also inhibited by this agent [Heiniich, J. E., L. A. Hunsaker, and D. L. Vanda Jagt, IRCS Med. Sci., 11: 304 (1983)].

The study of anticancer activity of gossypol was first reported in 1975, using the leukemia P-388 system [Joland, S. D., R. M. Wiedhaph, and J. R. Cole, J. Pharm. Sci., 64: 1889 (1975)]. More recently, this compound has shown differential cytotoxic effects in human melanoma, colon carcinoma, mammary adenocarcinoma [Rao, P. N., Y-C. Wang, E. Lotzova, A. A. Khan, S. P. Rao and L. C. Stephens, Cancer Chemother. Pharmacol., 15: 20 (1985)] and other tissue culture cell lines [Tuszynsk, G. P., and G. Cussu, Cancer Res., 44: 768 (1984)]. Gossypol is also found to be a potent hyperthermic sensitizer of HeLa cells [Kim, S. H., J. H. Kim, A. A. Alfieri, S. Q. He, and C. W. Young, Cancer Res., 45: 6338 (1985)].

Certain of the compounds disclosed and claimed in the subject application were initially disclosed by the inventors in their article entitled "Anti-Fertility and Other Actions of Gossypol Analogues" and co-authored by M. Sonenberg, J-T. Huang, Y-F. Ren, T-L. Su, K. A. Watanabe, H. C. Haspel, R. E. Corin, and A. P. Hoffer, Contraception, March 1988, Volume 37, Number 3. This article was first mailed to subscribers of Contraception on Apr. 4, 1988.

During the course of studies on the structure-activity relationships of gossypol analogs, the inventors of the subject invention discovered a novel reaction which made it possible to synthesize chemicals having structures quite unrelated to gossypol, yet demonstrating gossypol-like biological activities. This process and the structures produced thereby constitute the present invention.

SUMMARY OF THE INVENTION

This invention concerns compounds having the structure:

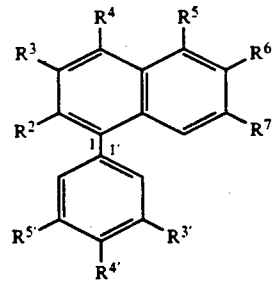

wherein each of $R^2$, $R^3$, $R^4$, $R^5$, $R^6$, $R^7$, $R^{2'}R^{3'}$, $R^{4'}$, and $R^{5'}$, is independently hydrogen (—H), or a hydroxyl (—OH), methoxy (—OMe), methyl (—Me), carboxaldehyde (—CHO) or phenylformazen (Ph—N=CH—) group.

This invention also provides a novel process of synthesizing the compounds of the subject invention, including intermediate compounds useful in the process.

The present invention also provides pharmaceutical compositions comprising a pharmaceutically effective amount of a compound according to the subject invention and a pharmaceutically acceptable carrier. Finally, the invention provides spermicidal methods and methods of killing or of retarding the proliferation of, cancer cells.

DETAILED DESCRIPTION OF THE INVENTION

Figure 1:
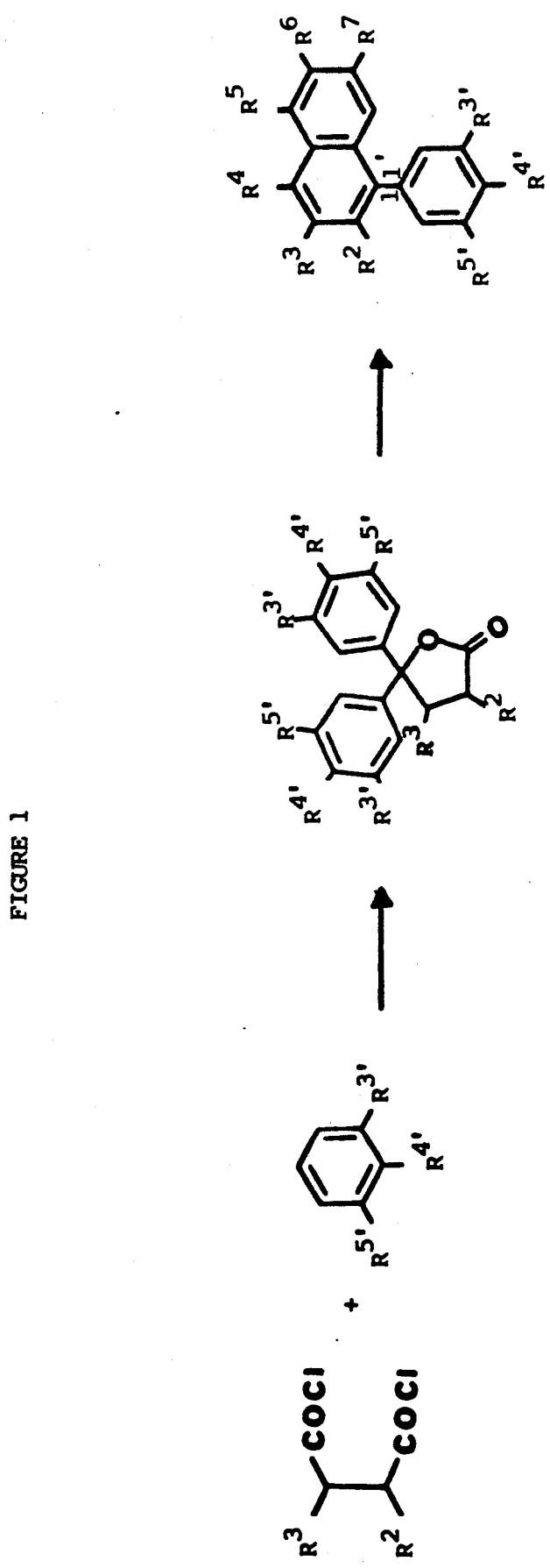
FIG. 1: Synthesis of compounds having structure I. Compounds having structures II and III are contacted to yield compounds having structure IV. Compounds having structure IV are then treated to yield compounds having structure I.

The subject invention provides a compound having the structure:

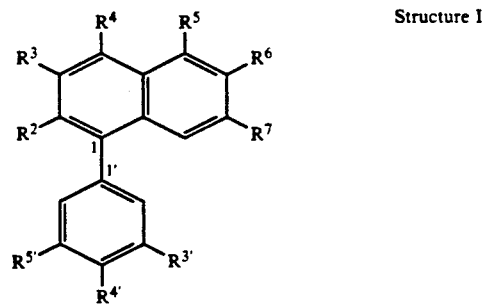

Structure I wherein each of $R^2$, $R^3$, $R^4$, $R^5$, $R^6$, $R^7$, $R^{3'}$, $R^{4'}$, and $R^{5'}$, is independently hydrogen, (—H) hydroxyl (—OH), methyl (—Me), methoxy (—OMe), carboxaldehyde (—CHO) or a phenylformazen (Ph—N=CH—) group.

Compounds of this structure may be used to produce a spermicidal effect. Also, these compounds may be used to kill or retard the proliferation of cancer cells.

A compound of the above identified structure may be selected from the group consisting of:
- 4-Hydroxy-1-phenylnaphthalene,
- 1-(4-Hydroxyphenyl)-4,6-dihydroxynaphthalene,
- 1-(4-Methylphenyl)-4-hydroxy-6-methylnaphthalene,
- 1-(3-Hydroxy-4-methylphenyl)-4,6-dihydroxy-7-methylnaphthalene,
- 1-(4-Hydroxy-3-methylphenyl)-4,7-dihydroxy-6-methylnaphthalene,
- 1-(3,4-Dimethylphenyl)-4-hydroxy-6,7-dimethylnaphthalene,
- 1-(3,4-Dihydroxyphenyl)-4,6,7-trihydroxynaphthalene,
- 1-(3,4,5-Trimethylphenyl)-4-hydroxy-5,6,7-trimethylnaphthalene,
- 1-(3,4,5-Trihydroxyphenyl)-4,5,6,7-tetrahydroxynaphthalene,
- 1-(4-Hydroxy-3,5-dimethylphenyl)-4,6-dihydroxy-5,7-dimethylnaphthalene,
- 1-(3,5-Dihydroxy-4-methylphenyl)-4,5,7-trihydroxy-6-methylnaphthalene,
- 1-(3,4-Dihydroxy-5-methylphenyl)-4,6,7-trihydroxy-5-methylnaphthalene,
- 4-Hydroxy-2,3-dimethyl-1-phenylnaphthalene,
- 1-(4-Hydroxyphenyl)-4-hydroxy-2,3,6-trimethylnaphthalene,
- 1-(4-Methylphenyl)-4-hydroxy-2,3,6-trimethylnaphthalene,
- 1-(4-Hydroxy-3-methylphenyl)-4,6-dihydroxy-2,3,7-trimethylnaphthalene,
- 1-(3-Hydroxy-4-methylphenyl)-4,7-dihydroxy-2,3,6-trimethylnaphthalene,
- 1-(3,4-Dimethylphenyl)-4-hydroxy-2,3,6,7-tetramethylnaphthalene,
- 1-(3,4-Dihydroxyphenyl)-4,6,7-triphenyl-2,3-dimethylnaphthalene,
- 1-(3,4,5-Trimethylphenyl)-4-hydroxy-2,3,5,6,7-pentamethylnaphthalene,
- 1-(3,4,5-Trihydroxyphenyl)-4,5,6,7-tetrahydroxy-2,3-dimethylnaphthalene,
- 1-(4-Hydroxy-3,5-dimethylphenyl)-4,6-dihydroxy-2,3,5,7-tetramethylnaphthalene,
- 1-(3,5-Dihydroxy-4-methylphenyl)-4,5,7-trihydroxy-2,3,6-trimethylnaphthalene, and
- 1-(3,4-Dihydroxy-5-methylphenyl)-4,6-7-trihydroxy-2,3,5-trimethylnaphthalene.

A compound of the above-identified structure may also be selected from the group consisting of:
- 4-Hydroxy-1-phenyl-3-phenylazomethynylnaphthalene,
- 4,6-Dihydroxy-1-(4-hydroxyphenyl)-3-phenylazomethynylnaphthalene,
- 4-Hydroxy-6-methyl-1-(4-methylphenyl)-3-phenylazomethynylnaphthalene,
- 4,6-Dihydroxy-1-(4-hydroxy-3-methylphenyl)-7-methyl-3-phenylazomethynylnaphthalene,
- 4-Hydroxy-6,7-dimethyl-1-(3,4-dimethylphenyl)-3-phenylazomethynylnaphthalene,
- 4,6,7-Trihydroxy-1-(3,4-dihydroxyphenyl)-3-phenylazomethynylnaphthalene,
- 4-Hydroxy-5,6,7-trimethyl-1-(3,4,5-trimethylphenyl)-3-phenylazomethynylnaphthalene,
- 4,5,6,7-Tetrahydroxy-1-(3,4,5-trihydroxyphenyl)-3-phenylazomethynylnaphthalene,
- 4,6-Dihydroxy-1-(4-hydroxy-3,5-dimethylphenyl)-5,7-dimethyl-3-phenylazomethynylnaphthalene,
- 4,5,7-Trihydroxy-1-(3,5-dihydroxy-4-methylphenyl)-6-methyl-3-phenylazomethynylnaphthalene, and
- 4,6,7-Trihydroxy-1-(3,4-dihydroxy-5-methylphenyl)-5-methyl-3-phenylazomethynylnaphthalene.

Further, the subject invention provides for a compound of the above-identified structure selected from the group consisting of:
- 4-Hydroxy-1-phenyl-2,3-bis(phenylazomethynyl)naphthalene,
- 4,6-Dihydroxy-1-(4-hydroxyphenyl)-2,3-bis(phenylazomethynyl)naphthalene,
- 4-Hydroxy-6-methyl-1-(4-methylphenyl)-2,3-bis(phenylazomethynyl)naphthalene,
- 4,6-Dihydroxy-1-(4-hydroxy-3-methylphenyl)-7-methyl-2,3-bis(phenylazomethynyl)naphthalene,
- 4,7-Dihydroxy-1-(3-hydroxy-4-methylphenyl)-6-methyl-2,3-bis(phenylazomethynyl)napthalene,
- 4-Hydroxy-6,7-dimethyl-1-(3,4-dimethylphenyl)-2,3-bis(phenylazomethynyl)naphthalene,
- 4,6,7-Trihydroxy-1-(3,4-dihydroxyphenyl)-2,3-bis(phenylazomethynyl)naphthalene,
- 4-Hydroxy-5,6,7-trimethyl-1-(3,4,5-trimethylphenyl)-2,3-bis(phenylazomethynyl)naphthalene,
- 4,5,6,7-Tetrahydroxy-1-(3,4,5-hydroxyphenyl)-2,3-bis(phenylazomethynyl)naphthtalene,
- 4,6-Dihydroxy-1-(4-hydroxy-3,5-dimethylphenyl)-5,7-dimethyl-2,3-bis(phenylazomethynyl)naphthalene,
- 4,5,7-Trihydroxy-1-(3,5-dihydroxy-4-methylphenyl)-6-methyl-2,3-bis-(phenylazomethynyl)naphthalene, and
- 4,6,7-Trihydroxy-1-(3,4-dihydroxy-5-methylphenyl)-5-methyl-2,3-bis-(phenylazomethynyl)naphthalene.

Moreover, the subject invention provides for a compound of the above-identifed structure selected from the group consisting of:
- 3-Formyl-4-hydroxy-1-phenylnaphthalene,
- 3-Formyl-4,6-dihydroxy-1-(4-hydroxyphenyl)naphthalene,
- 3-Formyl-4-hydroxy-6-methyl-1-(4-methylphenyl)naphthalene,
- 3-Formyl-4,6-dihydroxy-1-(4-hydroxy-3-methylphenyl)-7-methylnaphthalene,
- 3-Formyl-4,7-dihydroxy-1-(3-hydroxy-4-methylphenyl))-6-methylnaphthalene,
- 3-Formyl-4-hydroxy-6,7-dimethyl-1-(3,4-dimethylphenyl)naphthalene,
- 3-Formyl-4,6,7-trihydroxy-!-(3,4-dihydroxyphenyl)naphthalene,
- 3-Formyl-4-hydroxy-5,6,7-trimethyl-!-(3,4,5-trimethylphenyl)naphthalene,
- 3-Formyl-4,5,6,7,-tetrahydroxy-1-(3,4,5-trihydroxyphenyl)naphthalene,
- 3-Formyl-4,6-dihydroxy-1-(4-hydroxy-3-methylphenyl)-5,7-dimethylnaphthalene,
- 3-Formyl-4,5,7-trihydroxy-1-(3,5,-dihydroxy-4-methylphenyl)-6-methylnaphthalene, and
- 3-Formyl-4,6,7-trihydroxy-1-(3,4-dihydroxy-5-methylphenyl)-5-methylnaphthalene.

Lastly, a compound of the above-identified structure may be selected from the group consisting of:
- 2,3-Diformyl-4-hydroxy-1-phenylnaphthalene,
- 2,3-Diformyl-4,6-dihydroxy-1-(4-hydroxyphenyl)naphthalene, 2,3-Diformyl-4-hydroxy-6-methyl-1-(4-methyl-phenyl)naphthalene,
2,3-Diformyl-4,6-dihydroxy-1-(4-hydroxy-3-methylphenyl)-7-methylnaphthalene,
2,3-Diformyl-4,7-dihydroxy-1-(3-hydroxy-4-methylphenyl)-6-methylnaphthalene,
2,3-Diformyl-4-hydroxy-6,7-dimethyl-1-(3,4-dimethylphenyl)naphthalene,
2,3-Diformyl-4,6,7-trihydroxy-1-(3,4-dihydroxyphenyl)naphthalene,
2,3-Diformyl-4-hydroxy-5,6,7-trimethyl-1-(3,4,5-trimethylphenyl)naphthalene,
2,3-Diformyl-4,5,6,7-tetrahydroxy-1-(3,4,5-trihydroxyphenyl)naphthalene,
2,3-Diformyl-4,6-dihydroxy-1-(4-hydroxy-3,5-dimethylphenyl)-5,7-dimethylnapthalene,
2,3-Diformyl-4,5,7-trihydroxy-1-(3,5-dihydroxy-4-methylphenyl)-6-methylphenyl)-6-methylnaphthalene, and
2,3-Diformyl-4,6,7-trihydroxy-1-(3,4-dihydroxy-5-methylphenyl)-5-methylnaphthalene.

The subject invention also provides a unique intermediate compound having the structure:

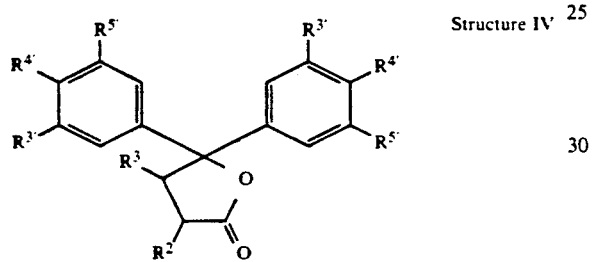

Structure IV wherein, each of $R^2$, $R^3$, $R^{3'}$, $R^{4'}$, and $R^{5'}$ is independently hydrogen or a methyl or methoxy group.

This invention provides a compound of the above-identified intermediate structure selected from the group consisting of:
4,4-Bis(phenyl)butyrolactone,
4,4-Bis(4-methylphenyl)butyrolactone,
4,4-Bis(4-methoxy-3-methylphenyl)butyrolactone,
4,4-Bis(3,4-dimethylphenyl)butyrolactone,
4,4-Bis(3,4,5-trimethylphenyl)butyrolactone,
4,4-Bis(4-methyoxyphenyl)butyrolactone,
4,4-Bis(3,4-dimethoxyphenyl)butyrolactone,
4,4-Bis(3,4,5-trimethoxyphenyl)butyrolactone,
4,4-Bis(4-methoxy-3,5-dimethylphenyl)butyrolactone,
4,4-Bis(3,5-dimethoxy-4-methylphenyl)butyrolactone,
4,4-Bis(4,5-dimethoxy-3-methylphenyl)butyrolactone,
2,3-Dimethyl-4,4-bis(phenyl)butyrolactone,
2,3-Dimethyl-4,4-bis(4-methylphenyl)butyrolactone,
2,3-Dimethyl-4,4-bis(3,4-dimethylphenyl)butyrolactone,
2,3-Dimethyl-4,4-bis(3,4,5-trimethylphenyl)butyrolactone,
4,4-Bis(4-methoxyphenyl)-2,3-dimethylbutyrolactone,
4,4-Bis(4-methoxy-3-methylphenyl)-2,3-dimethylbutyrolactone,
4,4-Bis(3,4-dimethoxyphenyl)-2,3-dimethylbutyrolactone,
4,4-Bis(3,4,5-Trimethoxyphenyl)-2,3-dimethylbutyrolactone,
4,4-Bis(4-methoxy-3,5-dimethylphenyl)-2,3-dimethylbutyrolactone,
4,4-Bis(3,5-dimethoxy-4-methylphenyl)-2,3-dimethylbutyrolactone, and
4,4-Bis(4,5-dimethoxy-3-methylphenyl)-2,3-dimethylbutyrolactone, This invention provides a method of producing a compound of the first-identified structure which comprises:
a) contacting a compound having the structure:

Structure II wherein each of $R^2$ and $R^3$, is hydrogen, or a methyl or methoxy group with a compound having the structure:

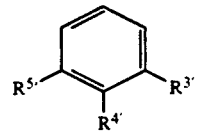

Structure III wherein each of $R^{3'}$, $R^{4'}$, and $R^{5'}$, is hydrogen, or a methyl or methoxy group to obtain a compound having the structure:

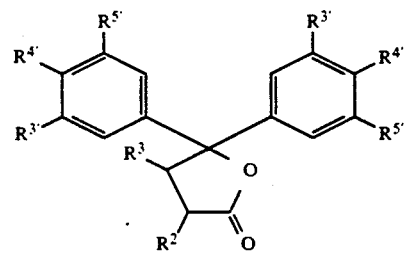

wherein each of $R^2$, $R^3$, $R^{3'}$, $R^{4'}$, and $R^{5'}$, is hydrogen, or a methyl or methoxy group;
b) treating the compound obtained in step (a) to produce a compound having the structure:

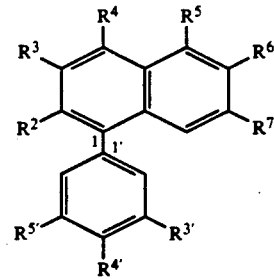

wherein each of $R^2$, $R^3$, $R^4$, $R^5$, $R^6$, $R^6$, $R^7$, $R^{3'}$, $R^{4'}$, and $R^{5'}$ is hydrogen or a hydroxyl, methoxy, methyl, carboxaldehyde, or phenylformazen group; and
c) recovering the resulting compound.

In the preferred embodiment the contacting of step (a) comprises condensation under Friedel-Crafts conditions. Most preferably, the condensation is effected in the presence of a Friedel-Crafts catalyst. One skilled in the art may obtain these results using other conditions. However, a Friedel-Crafts reaction provides the most direct approach to this synthesis.

In the preferred embodiment compounds of structures II and III are contacted and condensed under Friedel-Crafts conditions. Under controlled conditions, the reaction may be lead in the unusual direction forming 4,4-disubstituted-butyrolactones of structure IV, instead of affording the corresponding 1,4-disubstituted-butan-1, 4-diones. The reaction is preferably carried out in an inert solvent such as chlorinated hydrocarbon, most preferably ethane tetrachloride, in the presence of a Friedel-Crafts catalyst, such as aluminium chloride, at a temperature range of from about $-5°$ C. to about $25°$ C. for a period of from 2 hours to 3 days.

One skilled in the art would be able to use any number of Friedel-Crafts catalysts, e.g. Lewis Acids such as $BF_3$ and $SnCl_4$ and would be able to vary the solvent.

In step (b) of the synthesis compounds of structure IV are treated to produce the compound of structure I.

In the preferred embodiment, the treating of step (b) comprises the addition of a Lewis acid and most preferred Lewis acid is boron tribromide.

In the preferred method of the subject invention, the treating of step (b) is effected in an inert solvent, more preferably, a chlorinated hydrocarbon, and most preferably ethane tetrachloride.

The treating of step (b) is effected at a temperature from about $-78°$ C. to about $25°$ C. and is preferably performed for a period from about 2 hours to about 24 hours.

Wherein the treating of step (b) comprises an intramolecular Friedel-Crafts reaction, the most efficient reaction is realized.

In the above product wherein $R^2$ and $R^3$, are hydrogen the product can be further modified by treatment with N, N'-diphenylformamidine to give the Schiff's base mono-($R^2$) or di-($R^2$, $R^3$) phenylazomethynylnaphthalene which can be hydrolyzed in an acid such as sulfuric acid to give the corresponding carboxaldehyde.

The subject invention also provides a pharmaceutical composition which comprises a pharmaceutically effective amount of a compound of structure I or a pharmaceutically acceptable alkali or alkali earth metal addition salt thereof and a pharmaceutically acceptable carrier.

The term "pharmaceutically acceptable carrier" encompasses any of the standard pharmaceutical carriers such as sterile solutions, tablets, coated tablets and capsules. Typically such carriers, contain excipients such as starch, milk, sugar, certain types of clay, gelatin, steric acid, talc, vegetable fats or oils, gums, glycols, or other known excipients. Such carriers may also include flavor and color additives or other ingredients. Compositions comprising such carriers are formulated by well known conventional methods. However, the compositions comprising the compound of structure I or an alkali or alkali earth metal salt thereof, are previously unknown.

This invention further concerns a method of treating sperm so as to render the sperm incapable of fertilization which comprises contacting the sperm with a spermicidal amount of a compound of structure I.

The amount of the compound required will vary considerably depending upon conditions. However, these amounts are readily determinable by one skilled in the art.

Additionally, this invention provides a method of sterilizing a subject which comprises administering to the subject a spermicidally effective amount of the pharmaceutical composition described above.

In this method, the administration of the compound may be effected by any of the well known methods, including but not limited to oral, intravenous, intramuscular, and subcutaneous. The method of delivery, the amount to be used and the frequency of delivery, are expected to vary according to the situations, the carrier used, and result desired. However, those variables are readily determinable by one skilled in the art.

The term "subject" includes but is not limited to domestic animals and human beings.

Lastly, the subject invention provides a method of killing, or of retarding the proliferation, of, cancer cells which comprises contacting the cells with an effective antitumor amount of a compound of structure I.

In the preferred embodiment the cancer cells comprises human melanoma, colon carcinoma, or mammary adenocarcinoma cells.

The following examples are illustrative of the process and products of the subject invention, but are not to be construed as limiting.

EXAMPLE 1

A well-stirred mixture of veratrole (220 g, 1.6 mol) and aluminum chloride (110 g. 0.83 mol) in ethylene chloride (1 L) is cooled to $-5°$ C. Succinyl chloride (80 g, 0.52 mol) is slowly added to the mixture at $-5°$ C. over a period of 2 hours. After completion of the addition, the mixture is allowed to warm to room temperature, and the stirring is continued for 2 days. The reaction is quenched by addition of a mixture of ice (200 g) and concentrated hydrochloric acid (30 mL). The organic layer is separated, washed successively with water, saturated aqueous sodium bicarbonate solution and water, and dried over sodium sulfate. After concentration in vacuo, the residue is crystallized from toluenechloroform to give 42.5 g (23%) of 4,4-bis(3,4-dimethoxyphenyl) butyrolactone, mp $133°-134°$ C. Infrared specture in KBr, 1765 $cm^{-1}$ for lactone, $^1H$ NMR ($CDCl_3$) $\delta 6.86$ (6H, m, aromatic H), 3.85 (12H, ds, $4 \times OMe$), 2.66 (4H, m, $-CH_2CH_2-$).

Microanalyses calculated from $C_{20}H_{22}O_6$: C, 67.03; H, 5.19%. Found: C, 67.08; H, 6.24%.

EXAMPLE 2

A solution of boron tribromide (20 g. 80 mmol) in methylene chloride (20 mL) is added dropwise to a vigorously stirred solution of 4,4-bis(3,4-dimethoxyphenyl)butyrolactone (10.0 g. 27.9 mmol) in methylene chloride (200 mL) at $-78°$ C. Stirring is continued for 3 hours at $78°$ C., and then at room temperature overnight. Ice (100 g) is added to the mixture, and organic layer is separated. The aqueous layer is extracted with ethyl acetate ($3 \times 100$ mL). The combined organic solutions are dried over sodium sulfate, and concentrated in vacuo. The residue is chromatographed over a silica gel colum using a mixture of chloroform and ethanol (98:2 v/v) as the eluent to give 1-(3,4-di-hydroxyphenyl)-4,6,7-trihydroxynaphthalene (4.5 g. 53%), mp $224°-226°$ C. $^1H$ NMR ($Me_2SO-d_6$) $\delta 9.6-8.8$ (5H, m, OH, exchangeable), 7.4-6.5 (7H, m, aromatic H).

Microanalyses calculated for $C_{16}H_{12}O_5 \cdot \frac{1}{2}H_2O$: C, 64.54; H, 4.57%. Found: C, 64.17; H, 4.37%.

EXAMPLE 3

A mixture of 1-(3,4-dihydroxyphenyl)-4,6,7-trihydroxynaphthalene (1.0 g. 3.4 mmol) and N,N,-diphenylformamidine (6.2 g. 32 mmol) is finely pulverized, and is fused under nitrogen for 2.5 hours at 130° C. After cooling to room temperature, the solid mixture is dissolved in a minimal amount of methylene chloride, and chromatographed over a silica gel column using a mixture of methylene chloride and ethanol (95:1 v/v) as the eluent to give 1-(3,4-dihydroxyphenyl)-4,6,7-trihydroxy-3-phenylazomethynylnaphthalene (0.33 g., 28%, after crystallization from cchloroformacetone) as red crystals, mp 208°-210° C. $^1$H NMR (Me$_2$SO-d$_6$) δ9.8-8.8 (6H, m, OH and -CH=N-), 7.7-6.6 (11H, m, aromatic H).

Microanalysis, calculated for C$_{23}$H$_{17}$NO$_5$: C, 71.31; H, 4.42; N, 3.62. Found: C, 71.24; H, 4.21; N, 3.53%.

EXAMPLE 4

A mixture of 4,6,7-trihydroxymethyl-1-(3,4-dihydroxyphenyl)-naphthalene (100 mg. 0.34 mmol) and N,N,-di-phenylformamidine (1.0 g. 5.1 mmol) is evenly pulverize, and then is fused in a nitrogen atmosphere at 156°-160° C. for 2 hours. The mixture, after cooling to room temperature, is dissolved in minimal amount of methylene chloride and chromatographed over a silica gel column using methylene chloride and chromatographed over a silica gel column using methylene chloride and chromatographed over a silica gel column using methylene chloride-ethanol (95:5 v/v) as the eluent to give 4,6,7-trihydroxy-1-(3,4-dihydroxyphenyl)-2,3-bis(phenylazomethynyl)-naphtalene (40 mg. 24%) a brown crystals after recrystallization from methylene chloride-acetone, mp 255°-257° C. $^1$H NMR (Me$_2$SO-d$_6$) δ 10.8 (1H, s, —CH=N—), 10.9-9.0 (5H, m, OH, exchangeable), 9.0 (1H, s, —CH=N—), 7.5-6.6 (15H, m, aromatic H).

Microanalyses, calculated for C$_{30}$H$_{22}$N$_2$O$_5$.3/2H$_2$O: C, 69.62; H, 4.87; N, 5.41%. Found: C, 69.67; H, 4.71; N, 5.75%.

EXAMPLE 5

A solution of 1-(3,4-dihydroxyphenyl)-4,6,7-trihydroxy-3-phenylazomethynylnaphthalene (80 mg, 0.21 mmol) in glacial acetic acid (10 mL) is cooled to 0.C. Concentrated sulfuric acid (5 mL) is added dropwise to the solution. After the addition, the mixture is heated at 90° C. for 5 minutes. Ice (100 g) is added, and the mixture is extracted with ethyl acetate (5×20 mL). The combined organic extracts are washed with water (2×40 mL), dried over sodium sulfate, and then concentrated in vacuo. The residue is chromatographed over a silica gel column using methylene chloride-methanol (92:8 v/v) as the eluent to give 1-(3,4-dihydroxyphenyl)-4,6,7-trihydroxy-3-formylnaphthalene (45 mg. 70%) as greenish yellow crystals, mp >300° C. $^1$H NMR (Me$_2$SO-d$_6$) δ10.12 (1H, s, CHO), 9.85-8.79 (5H, m, OH), 7.93-6.57 (6H, m, aromatic H).

Microanalyses. Calculated for C$_{17}$H$_{12}$O$_6$: C, 65.39; H, 3.87%. Found: C, 65.51; H, 3.82%.

DISCUSSION

The inventors have determined that 4,6,7-trihydroxy-1-3(3,4-dihydroxyphenyl)-3-(phenylazomethynyl)naphthalene demonstrates spermicidal activity as potent as gossypol in causing complete inhibition of motility within the first five minutes of co-incubation at a concentration of 50 μM. 4,6,7-Trihydroxy-1-(3,4-dihydroxyphenyl)-naphthalene also produced 100% inhibition after 40 minutes. The in vivo effects of co-precipitates of polyvinylpyrrolidone (PVP) and the above two compounds on testicular morphology were compared with those of PVP-saline and PVP-gossypol. PVP-gossypol caused morphological defects in the seminiferous epithelium very similar to those seen in rats made infertile with oral doses of gossypol. The subject compounds, however, did not cause significant morphological effects in the seminiferous epithelium in the testis injected with these agents. 4,6,7-Trihydroxy-1-(3,4-dihydroxypheny)-3-(phenylazomethynyl)-naphthalene and 4,6,7-trihydroxy-1-(3,4-di-hydroxyphenyl)naphthalene were found to be active against mouse leukemic L1210 cells in tissue culture (LD$_{50}$=5.50 and 9.65 μM, respectively) about one order of magnitude more active than gossypol (LD50 =57 μM) in parallel experiments in inhibiting these cells in tissue culture. The former naphthalene derivative was found to exhibit a heat sensitizing effect as potent as gossypol whereas the latter derivative showed little activity. Thus 4,6,7-trihydroxy-1-(3,4-dihydroxyphenyl)-3-(phenylazomethynyl)naphthalene and gossypol completely alleviated the HeLa S cells at 40 μM, at pH 7.4 and 6.7 for 4 hours at 37° C. Whereas, 79 and 93%, respectively, of the HeLa S cells survived in the presence of 40 μM concentration of 4,6,7-trihydroxy-1-(3,4-dihydroxyphenyl)naphthalene.

What is claimed is:

1. A compound having the structure:

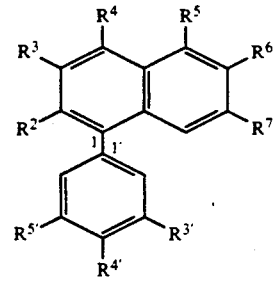

wherein each of R$^2$, R$^3$, R$^5$, R$^6$, R$^7$, R$^{3'}$, R$^{4'}$, and R$^{5'}$ is independently hydrogen, or a hydroxyl, methyl, methoxy, formyl or phenylazomethynl group and R$^4$ is a hydroxyl group with the proviso that at least one of R$^2$, R$^3$, R$^5$, R$^6$, R$^7$, R$^{3'}$, R$^{4'}$, or R$^{5'}$ is a formyl or a phenylazomethnyl group.

2. A compound selected from the group consisting of:
   1-(4'-Hydroxyphenyl)-4,6-dihydroxynaphthalene,
   1-(4'-Methylphenyl)-4-hydroxy-6-methylnaphthalene,
   1-(b 3'-Hydroxy-4-methylphenyl)-4,6-dihydroxy-7-methylnaphthalene,
   1-(4'-Hydroxy-3'-methylphenyl)-4,7-dihydroxy-6-methylnaphthalene,
   1-(3',4'-Dimethylphenyl)-4-hydroxy-6,7-dimethylnaphthalene,
   1-(3',4'-Dihydroxyphenyl)-4,6,7-trihydroxynaphthalene,
   1-(3',4',5'-Trimethylphenyl)-4-hydroxy-5,6,7-trimethylnaphthalene,
   1-(3',4',5'-Trimethylphenyl)-4,5,6,7-tetrahydroxynaphthalene,
   1-(4'-Hydroxy-3',5'-dimethylphenyl)-4,6-dihydroxy-5,7-dimethylnaphthalene,
   1-(3',5'-Dihydroxy-4'-methylphenyl)-4,5,7-trihydroxy-6-methylnaphthalene.
   1-(3',4'-Dihydroxy-5'-methylphenyl)-4,6,7-trihydroxy-5-methylnaphthalene,
   4-Hydroxy-2,3-dimethyl-1-phenylnaphthalene, 1-(4'-Hydroxyphenyl)-4-hydroxy-2,3,6-trimethyl-naphthalene.
1-(4'-Methylphenyl)-4-hydroxy-2,3,6-trimethylnaphthalene.
1-(4'-Hydroxy-3'-methylphenyl)-4,6-dihydroxy-2,3,7-trimethylnaphthalene,
1-(3'-Hydroxy-4'-methylphenyl)-4,7-dihydroxy-2,3,6-trimethylnaphthalene,
1-(3',4'-Dimethylphenyl)-4-hydroxy-2,3,6,7-tetramethylnaphthalene,
1-3',4'-Dihydroxyphenyl)-4,6,7-triphenyl-2,3-dimethylnaphthalene,
1-(3',4',5'-Trimethylphenyl)-4-hydroxy-2,3,5,6,7-pentamethylnaphthalene,
1-(3',4',5'-Trihydroxyphenyl)-4,5,6,7-tetrahydroxy-2,3-dimethylnaphthalene,
1-(4'-Hydroxy-3',5'-dimethylphenyl)-4,6-dihydroxy-2,3,5,7-tetramethylnaphthalene,
1-(3',5'-Dihydroxy-4'-methylphenyl)-4,5,7-trihydroxy-2,3,6-trimethylnaphthalene, and
1-(3',4'-Dihydroxy-5'-methylphenyl)-4,6,7-trihydroxy-2,3,5-trimethylnaphthalene.

3. A compound of claim 1 selected from the group consisting of:
4-Hydroxy-1-phenyl-3 phenylazomethynylnaphthalene,
4,6-Dihydroxy-1-(4'-hydroxyphenyl)-3-phenylazomethynylnaphthalene,
4-Hydroxy-6-methyl-1-(4'-methylphenyl)-3-phenylazomethynylnahthalene,
4,6-Dihydroxy-1-(4'-hydroxy-3'-methylphenyl)-7-methyl-3-phenylazomethynylnaphthalene,
4-Hydroxy-6,7-dimethyl-1-(3',4'-dimethylphenyl)-3-phenylazomethynylnaphthalene,
4,6,7-Trihydroxy-1-(3',4'-dihydroxyphenyl)-3-phenylazomethynylnaphthalene,
4-Hydroxy-5,6,7-trimethyl-1-(3',4',5'-trimethylphenyl)-3-phenylazomethynyl-naphthalene,
4,5,6,7-Tetrahydroxy-1-(3',4',5'-trihydroxyphenyl)-3-phenylazomethynylnaphthalene,
4,6-Dihydroxy-1-(4'-hydroxy-3',5'-dimethylphenyl)-5,7-dimethyl-3-phenylazomethynyl-naphthalene,
4,5,7-Trihydroxy-1-(3',5'-dihydroxy-4'-methylphenyl)-6-methyl-3-phenylazomethynyl-naphthalene, and
4,6,7-Trihydroxy-1-(3',4'-dihydroxy-5'-methylphenyl)-5-methyl-3-phenylazomethynyl-naphthalene.

4. A compound of claim 1 selected from the group consisting of:
4-Hydroxy-1phenyl-2,3-bis(phenylazomethynyl)-naphthalene,
4,6-Dihydroxy-1-(4'-hydroxyphenyl)-2,3-bis(-phenylazomethynyl)naphthalene,
4-Hydroxy-6-methyl-1-(4'-methylphenyl)-2,3-bis(-phenylazomethynyl)naphthalene,
4,6-Dihydroxy-1-(4'-hydroxy-3'-methylphenyl)-7-methyl-2,3-bis(phenylazomethylnyl)naphthalene,
4,7-Dihydroxy-1-(3'-hydroxy-4'-methylphenyl)-6-methyl-2,3,bis(phenylazomethynyl)naphthalene,
4-Hydroxy-6,7-dimethyl-1-(3',4'-dimethylphenyl)-2,3-bis(phenylazomethylnyl)naphthalene,
4,6,7-Trihydroxy-1-(3',4'-dihydroxyphenyl)-2,3-bis(-phenylazomethynyl)naphthalene,
4-Hydroxy-5,6,7-trimethyl-1-(3',4',5'-trimethylphenyl)-2,3-bis(phenylazomethynyl)-naphthalene,
4,5,6,7-Tetrahydroxy-1-(3',4'5'-hydroxyphenyl)-2,3-bis(phenylazomethynyl)-naphthtalene,
4,6-Dihydroxy-1-(4'-hydroxy-3',5'-dimethylphenyl)-5,7-dimethyl-2,3-bis(phenylazomethynyl)-naphthalene,
4,5,7-Trihydroxy-1-(3',5'-dihydroxy-4-methylphenyl)-6-methyl-2,3-bis-(phenylazomethynyl)-naphthalene, and
4,6,7-Trihydroxy-1-(3',4'-dihydroxy-5'-methylphenyl)-5-methyl-2,3-bis-(phenylazomethynyl)-naphthalene.

5. A compound of claim 1 selected from the group consisting of:
3-Formyl-4-hydroxy-1-phenylnaphthalene,
3-Formyl-4,6-dihydroxy-1-(4'-hydroxy-phenyl)naphthalene,
3-Formyl-4-hydroxy-6-methyl-1-(4'-methylphenyl)-naphthalene,
3-Formyl-4,6-dihydroxy-1-(4'-hydroxy-3-methylphenyl)-7-methylnaphthalene,
3-Formyl-4,7-dihydroxy-1-(3'-(3'-hydroxy-4'-methylphenyl))-6-methylnaphthalene,
3-Formyl-4-hydroxy-6,7-dimethyl-1-(3',4'-dimethylphenyl)naphthalene,
3-Formyl-4,6,7-trihydroxy-1-(3',4'-dihydroxyphenyl)naphthalene,
3-Formyl-4-hydroxy-5,6,7-trimethyl-1-(3',4',5'-trimethylphenyl)naphthalene,
3-Formyl-4,5,6,7,-tetrahydroxy-1-(3',4',5'-trihydroxyphenyl)naphthalene,
3-Formyl-4,6-dihydroxy-1-(4'-hydroxy-3'-methylphenyl)-5,7-dimethylnaphthalene,
3-Formyl-4,5,7-trihydroxy-1-(3',5',-dihydroxy-4'-methylphenyl)-6-methylnaphthalene, and
3-Formyl-4,6,7-trihydroxy-1-(3',4'-dihydroxy-5-methylphenyl)-5-methylnaphthalene.

6. A compound of claim 1 selected from the group consisting of:
2,3-diformyl-4-hydroxy-1-phenylnaphthalene,
2,3-diformyl-4,6-dihydroxy-1-(4-hydroxyphenyl)-naphthalene,
2,3-diformyl--4-hydroxy-6-methyl-1-(4-methylphenyl)naphthalene,
2,3-diformyl-4,6-dihydroxy-1-(4'-hydroxy-3'-methylphenyl)-7-methylnaphthalene,
2,3-diformyl-4,7-dihydroxy-1-(3'-hydroxy-4'-methylphenyl)-6-methylnaphthalene,
2,3-diformyl-4-hydroxy-6,7-dimethyl-1-(3',4'-dimethylphenyl)naphthalene,
2,3-diformyl-4,6,7-trihydroxy-1-(3',4'-dihydroxyphenyl)naphthalene,
2,3-Diformyl-4-hydroxy-5,6,7-trimethyl-1-(3',4',5'-trihydroxyphenyl)naphthalene,
2,3-diformyl-4,5,6,7-tetrahydroxy-1-(3',4',5-trihydroxyphenyl)naphthalene,
2,3-Diformyl-4,6-dihydroxy-1-(4'-hydroxy-3',5'-dimethylphenyl)-5,7-dimethylnaphthalene,
2,3-diformyl-4,5,7-trihydroxy-1-(340 ,5'-dihydroxy-4'-methylphenyl)-6-methylphenyl)-6-methylnaphthalene, and
2,3-diformyl-4,6,7-trihydroxy-1-(3',4'-dihydroxy-5'-methylphenyl)-5-methylnaphthalene.

7. A pharmaceutical composition which comprises a pharmaceutically effective amount of a compound of claims 1 or 2 or a pharmaceutically acceptable alkali or alkali earth metal addition salt thereof and a pharmaceutically acceptable carrier.

8. A method of treating sperm so as to render the sperm incapable of fertilization which comprises contacting the sperm with a spermicidal amount of a compound of claims 1 or 2.

9. A method of sterilizing a subject which comprises administering to the subject a spermicidally effective amount of the composition of claim 7.

10. A method of claim 8, wherein the subject is a domestic animal.

11. A method of claim 8, wherein the subject is a human being.

12. A method of killing, or of retarding the proliferation, of, cancer cells which comprises contacting the cells with an effective antitumor amount of a compound of claims 1 or 2.

13. A method of claim 12, wherein the cancer cells comprises human melanoma, colon carcinoma, or mammary adenocarcinoma cells.

* * * * *